(12) United States Patent
Hausmann et al.

(10) Patent No.: US 9,192,734 B2
(45) Date of Patent: Nov. 24, 2015

(54) HIGH-PRESSURE CHAMBER

(75) Inventors: Matthias Hausmann, Rees (DE); Thomas Wabnitz, Hattingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 483 days.

(21) Appl. No.: 13/383,600

(22) PCT Filed: Jun. 7, 2010

(86) PCT No.: PCT/EP2010/057937
§ 371 (c)(1),
(2), (4) Date: Feb. 6, 2012

(87) PCT Pub. No.: WO2011/006711
PCT Pub. Date: Jan. 20, 2011

(65) Prior Publication Data
US 2012/0174919 A1   Jul. 12, 2012

(30) Foreign Application Priority Data
Jul. 13, 2009   (EP) .................................... 09165311

(51) Int. Cl.
*A61M 15/00* (2006.01)
*A61M 11/02* (2006.01)
(Continued)

(52) U.S. Cl.
CPC ............. *A61M 15/009* (2013.01); *A61M 11/02* (2013.01); *A61M 11/06* (2013.01);
(Continued)

(58) Field of Classification Search
CPC ..................... A61M 11/02; A61M 2015/0035; A61M 2205/7545; A61M 11/06; A61M 15/009; A61M 2205/8281; B05B 11/3042; B05B 1/00; B05B 11/3015; B05B 15/008; B05B 11/3091; B05B 11/3001; A61B 17/3203

USPC ............ 128/200.11–200.24, 203.12, 203.15, 128/205.24; 239/562, 543, 544, 590–590.5, 239/553–533.5, 33, 349, 533.15, 571, 583; 222/385, 383.1, 401, 402, 402.1; 137/533, 533.17, 533.23

See application file for complete search history.

(56) References Cited

U.S. PATENT DOCUMENTS 3,502,035 A    3/1970   Fedit
5,472,143 A *  12/1995  Bartels et al. ................. 239/462
(Continued)

FOREIGN PATENT DOCUMENTS

CA   2513167 A1   10/2004
DE   1653651 A1   7/1971
(Continued)

OTHER PUBLICATIONS

International Search Report and Written Opinion for PCT/EP2010/057937 mailed Jul. 20, 2010.
(Continued)

*Primary Examiner* — Annette Dixon
(74) *Attorney, Agent, or Firm* — Michael P. Morris; Mary-Ellen M. Devlin

(57) ABSTRACT

The invention relates to a high-pressure chamber for preferably atomizing or injecting metered amounts of fluid, such as pharmaceutical preparations. The components of the high-pressure chamber determining the strength thereof are made of a sintered metal body having plastic regions directly attached thereto. The plastic regions allow corrosion resistance and material compatibility of the interior of the high-pressure chamber and fluids placed under pressure therein. The shape of the sintered metal body provides the entire system with the rigidity required for high-pressure operation and with directly molded connection elements prescribing the type of connection to other components. The components of the high-pressure chamber determining the strength thereof are thereby deformed or crimped to each other, so that inexpensive and quick overall assembly processes are available.

23 Claims, 5 Drawing Sheets

(51) Int. Cl.
*A61M 11/06* (2006.01)
*B05B 1/00* (2006.01)
*B05B 11/00* (2006.01)
*B05B 15/00* (2006.01)
*A61B 17/3203* (2006.01)

(52) U.S. Cl.
CPC ............ *A61M 15/0035* (2014.02); *B05B 1/00* (2013.01); *B05B 11/3001* (2013.01); *B05B 11/3042* (2013.01); *B05B 15/008* (2013.01); *A61B 17/3203* (2013.01); *A61M 2205/7545* (2013.01); *A61M 2205/8281* (2013.01); *B05B 11/3015* (2013.01); *B05B 11/3091* (2013.01); *Y10T 29/49826* (2015.01); *Y10T 29/49908* (2015.01)

(56) References Cited

U.S. PATENT DOCUMENTS

| | | | | |
|---|---|---|---|---|
| 5,868,287 | A  * | 2/1999 | Kurokawa et al. | 222/380 |
| 6,548,647 | B2 * | 4/2003 | Dietz et al. | 534/582 |
| 7,837,235 | B2 * | 11/2010 | Geser et al. | 285/332.2 |
| 2002/0176788 | A1 | 11/2002 | Moutafis et al. | |
| 2004/0134824 | A1 * | 7/2004 | Chan et al. | 206/524.1 |
| 2005/0194472 | A1 * | 9/2005 | Geser et al. | 239/602 |
| 2009/0060764 | A1 | 3/2009 | Mitzlaff et al. | |

FOREIGN PATENT DOCUMENTS

| | | |
|---|---|---|
| DE | 102004031673 A1 | 1/2006 |
| JP | 2001346878 A | 12/2001 |
| JP | 2005511210 A | 4/2005 |
| JP | 2007517529 A2 | 7/2007 |
| WO | 9407607 A1 | 4/1994 |
| WO | 03049786 A2 | 6/2003 |
| WO | 2004089551 A2 | 10/2004 |
| WO | 2006126014 A2 | 11/2006 |

OTHER PUBLICATIONS

Chen, F-K et al., "A study of forming pressure in the tube-hydroforming process". Journal of Materials Processing Technology, 192-193, 2007, p. 404-409.

* cited by examiner

PRIOR ART

PRIOR ART

HIGH-PRESSURE CHAMBER

FIELD OF THE INVENTION

The present invention relates to a high pressure chamber which is made up of a plurality of individual parts and is operated by liquid.

BACKGROUND OF THE INVENTION

It is known that in most medical procedures in which liquids are administered to a patient's body or are conveyed inside technical medical equipment, very low pressures are used, for example when setting up infusions or in medical procedures in which blood or other physiological liquids are circulated. Conventional dispensing systems for cosmetics or medical pressurised gas atomisers also generally operate at below 7 bar of liquid pressure, very rarely up to 20 bar. High pressure pumping systems, on the other hand, are generally known from various industrial applications but are not really suitable for use in technical medical equipment as they are often made of materials that are not compatible with the particular medical active substances or may even release substances that are toxic to the patients. Often, with technical medical components, it is essential that they are sterilizable. Because of the hygiene requirements imposed, components for medical equipment are generally designed for brief periods of use or even single use, so that in this field the demands for mass production are significantly increased. Moreover, industrial pumping systems are often of a mechanically complex nature so that it is difficult to reduce them to the size of handheld medical equipment, in particular.

In the treatment of lung diseases, in the meantime, the use of portable handheld equipment has become indispensable. Using such equipment therapies can be given daily, even at a distance from the practice of the doctor providing the treatment, and in this way a patient can always have access to an essential emergency medication for inhalation.

When a liquid medicament formulation is nebulised a precisely metered amount of active substance is intended to be converted into an aerosol for inhalation. The aerosol should have a small average particle size with a small droplet size distribution. In order to achieve this using nozzle pump arrangements without the use of propellants, pressures of 100-1200 bar are required in the associated pump chambers, with high demands on the leak-tight construction of the system.

By the term "medicament formulation" is meant, in the present invention, apart from medicaments, therapeutic agents or the like, particularly every kind of agent for inhalation or other forms of administration.

However, the invention is not restricted to medical nebulisation but may be used across different sectors for dispensing all kinds of liquids under pressure, for example when dispensing measured amounts of liquid in injectors, spray systems and other dispensing systems and in systems in which jets of liquid under high pressure are used (e.g. in cutting systems), even though the description that follows is directed primarily to medical applications and the preferred nebulisation of a medicament formulation for inhalation. Moreover, high pressure chambers of this kind and the manufacturing techniques associated with them may be used in totally different industrial fields such as the motor industry, for example, although this invention relates primarily to pumping situations in which particularly clean handling of the liquid in question is essential, as for example in medical technology in the pharmaceutical industry or food technology.

WO 91/14468 A1 and WO 97/12687 A1 describe nebulisers or miniaturised high pressure nebulisers. These comprise as the reservoir for a medicament preparation that is to be nebulised an insertable rigid container with an inner bag and a manually operated pressure generator with a drive spring for conveying and nebulising the medicament preparation. A container of this kind, as disclosed in WO 96/06011 A1 and WO 00/49988 A2, holds a volume of about 2-10 ml. An alternative nebuliser to those mentioned above has become known from the prior art in the meantime and is shown by way of example in FIG. 1 and described in detail hereinafter. In this nebuliser, a multipart pumping chamber is used. The strength-determining components of this substantially circular cylindrical pumping chamber are a guide tube for the pumping piston which is guided in a longitudinally movable manner, at the reservoir end a support ring which is fixed by a screwed-on cap-like retaining element and, at the other end of the pumping chamber, a nozzle holder fixed by a similar screwed-on cap-like retaining element. Details of possible microstructures for the expulsion nozzle held by the nozzle holder are disclosed in the specifications WO 94/07607, WO 99/16530 and WO 2005/000476 A1.

The components used for the pump chamber are subject to particular requirements regarding the strength of the material. Often, they cannot be made of the comparatively cheap plastics that are otherwise conventional for mass produced components in medical technology. The retaining elements described are typically metal components manufactured on lathes.

US 2002/0176788 shows, inter alia, a high pressure pump body the wall of which consists of thin walled tubing and in which the strength-determining components are not screwed together but joined to connecting elements by means of a crimped sealing bead. An outlet valve with sealing elements is inserted in the thin walled tubing. The tubing is pressed into a suitable recess in the valve unit so as to engage in a positively locking manner. When the high pressure envisaged is reached in the high pressure pumping body the corresponding valve opens and allows the liquid to flow continuously to the pump outlet.

The problem on which the present invention is based is to provide a high pressure chamber with an integrated outlet nozzle, particularly for medical nebuliser or injector systems, which is suitable for industrial manufacture. Systems of this kind deliver a metered amount of liquid in short pulses. The liquid is sucked in without the use of pressure and within a short time is brought to a peak pressure in the high pressure chamber at which the liquid is dispensed (preferably directly) through a nozzle. The sealing requirements for a pulsed system of this kind have not only static but also dynamic aspects compared with continuous pumping, which means that the connecting technology, particularly between the high pressure chamber and the outlet nozzle, is subject to particular demands.

By the term high pressure chamber is meant here a chamber that is substantially circular cylindrical on the inside, in which a fluid is put under pressure and expelled by the advancing of a piston or plunger.

SUMMARY OF THE INVENTION

This problem is solved according to the invention by a high pressure chamber in the form of a piston pump chamber made up of a plurality of components. The high pressure chamber has an inlet valve and an outlet nozzle. In the high pressure chamber a liquid is placed under high pressure and expelled through the outlet nozzle by means of an axially movable piston. At least one component consists of a metal component which is deformable and/or capable of being crimped and/or flanged and/or squeezed. The at least one component is connected to at least one other component of the chamber by positive locking, frictional locking and so as to be non-releasable. Advantageous further features are described hereinafter and in detail by reference to the figures.

The subject matter of the present invention relates to high pressure chambers for technical medical applications, such as for example in the nebulisation of liquid medicament formulations for administration into a patient's lungs or for injection into a patient's body.

As well as pure liquids and solutions the term "liquid" additionally encompasses dispersions, suspensions, suslutions (mixtures of solutions and suspensions) or the like. In particular, it relates to the aggregate state of the contents of the high pressure chamber during use.

One feature of the present invention is to configure the geometry of strength-determining components, for example, using special manufacturing processes described hereinafter, such that some components contain elements with which these components are joined to other components. These connecting elements may preferably be embodied as arms, strips, zig-zag rings (as in crown corks) or in other forms. The connecting elements are deformed or bent, preferably crimped, when two components are positively locked to one another. Preferably, a crimpable material is chosen for the component which is ductile and sufficiently deformable in the deformation range in the various geometries. A preferred material is one that solidifies in the deformed range after mechanical deformation. Joining components together by crimping enables the components to be assembled faster in comparison with screw connections, for example. Moreover, crimped joints are less prone to failure than screw connections in terms of their positional tolerances. Crimped joints are very robust and can be subjected to internal pressures of up to 5000 bar.

The strength-determining components of the high pressure chamber are preferably joined together at the end of the assembly process by crimping. This produces a component unit in which all the functional components of the system, such as for example, sealing elements, filter elements and nozzles, are enclosed.

The high pressure chamber described here is highly suitable for incorporation in handheld medical equipment by virtue of its very compact construction.

Another feature of the present invention is that metal components produced by metal injection moulding methods (MIM technology) are used as strength-determining components in high pressure chambers. The abbreviation MIM stands for metal injection moulding. The MIM process is a metal injection moulding process in which a metal powder (any of the known powdered metals and alloys may be used) is moulded with a binder, e.g. polyolefin, in the injection moulding process to produce the desired component and is then treated at different temperatures in a number of process steps. First the binder is removed from the component and then the component is hardened by sintering. As a rule, in the MIM process, metal powders with particle sizes of less than 30 microns and a median particle size distribution of 6-7 microns are used. This method can be used to produce components in mass production quantities on an economic scale. These components can be used without any further machining, e.g. on lathes. The geometry of the sintered metal components can be varied in numerous ways compared with conventionally manufactured metal components; thus the geometry of the sintered metal components is not restricted to rotationally symmetrical shapes, for example. In addition, by a suitable choice of starting powder, it is possible particularly to use corrosion resistant materials for the components, thus increasing the robustness of the system.

In a further feature of the present invention, plastic elements or plastic coatings are applied directly to strength-determining components of the high pressure chamber (preferably before reshaping or joining together). This can be achieved by a combination of manufacturing processes, for example using a component made of sintered metal as an insert in a plastics injection moulding process or a coating process (in the course of the plastics injection moulding process a further process insert is referred to as an "injection coated part", irrespective of the degree of surface coverage with plastics, but, in order to include other coating processes in the terminology, the term "base member" is used here). Similarly, metal components from other manufacturing or structuring processes may be used. In this way, different requirements of performance and function may advantageously be met with a single component.

The injection-coated metal components or base members have the rigidity needed for high pressure applications. By coating with plastics or attachment of plastics elements, depending on the position and contact with liquid and the choice of material, elastic sealing elements as well as pharmaceutical compatibility and corrosion proofing of the components can be achieved. Preferably all the surfaces of the components that are in direct contact with the liquid, i.e. particularly the surfaces inside the high pressure chamber, are coated, e.g. with polypropylene. This achieves compatibility between the component and active substance, in the case of sensitive active substances. Instead of polypropylene, depending on the desired effect, it is possible to coat elements or injection-coat the metal component with a plurality of standard commercial plastics selected from among the thermoplasts, duroplasts or elastomers.

Lining the interior of a sintered metal component with plastics, when it is used as a component of a pulse-operated high pressure chamber, has the further advantage that, depending on the choice of the metal powder for the injection moulding process, any open pores remaining in the sintered components are sealed and the surface is smoothed. In this way, even with coarse powders, it is possible to avoid increasing the inner volume of the high pressure chamber and hence the dead volume by pores in the surface of the sintered metal. The smaller the dead volume in a pumping system, the shorter the start-up phase of the system (in the description of a nebuliser this start-up phase is referred to hereinafter as priming) and the more accurate the metering of the liquid in pulsed systems.

The individual features of the present invention may be used largely independently of one another and/or combined with one another substantially as desired.

Further features and properties of the present invention will be explained in more detail in the description that follows and by reference to the drawings. In the drawings:

DETAILED DESCRIPTION OF THE INVENTION

Figure 1:
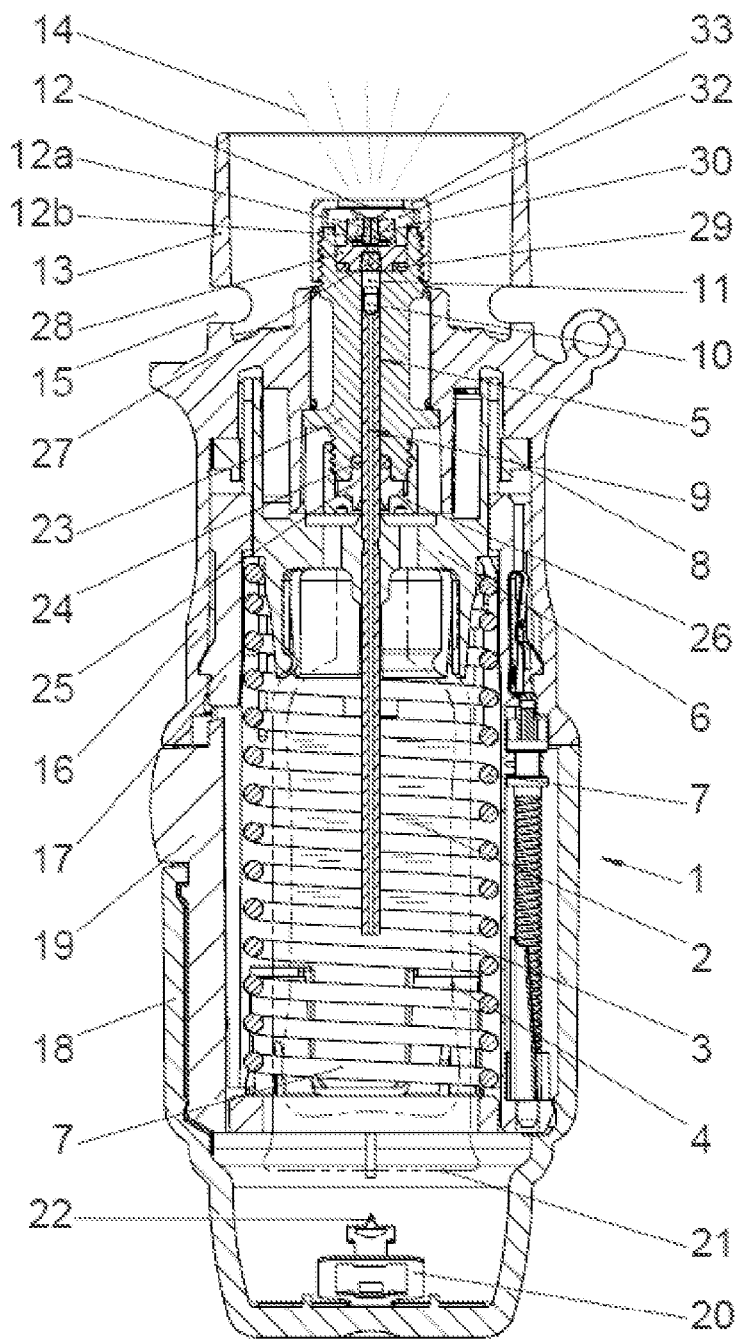
FIG. 1 is a schematic section through a known nebuliser in the non-tensioned state.
Figure 2:
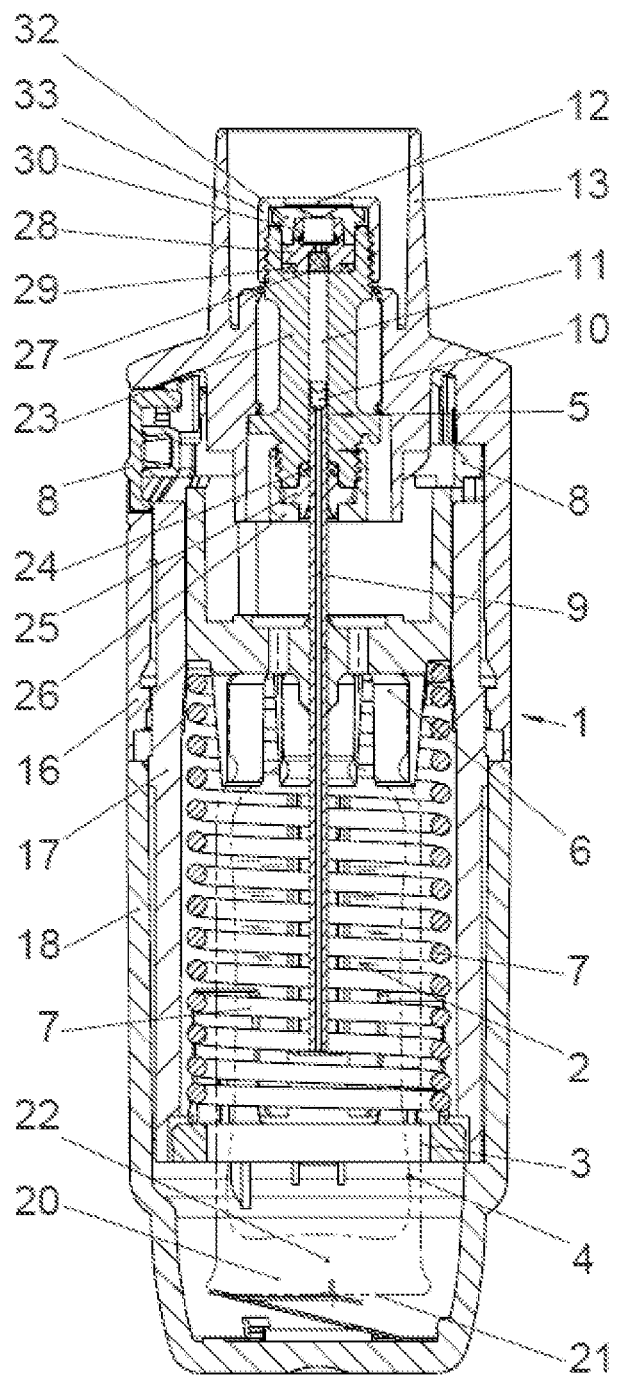
FIG. 2 is a schematic section though the known nebuiliser from FIG. 1 rotated through 90° compared with FIG. 1, in the tensioned state.

FIGS. 1 and 2 show in a schematic representation a known manually operated nebuliser (1) for nebulising a liquid (2), in which the pressure chamber (11) can be replaced by the proposed high pressure chamber. The nebuliser from FIG. 1 and (2) is a metering nebuliser which dispenses a given dose of liquid on each actuation cycle. During operation of the nebuliser a distinction is made between the untensioned state in which the metering volume in the pressure chamber (11) is unfilled (FIG. 1) and the tensioned state in which the pressure chamber (11) is filled (FIG. 2). The pressure chamber (11) corresponds in its function to a pumping chamber.

The strength-determining components of this pressure chamber are a central part (23) which is substantially cylindrical in its interior, for example made of a solid plastic such as, preferably, PEEK, a support ring (25) screwed to this central part (23) in the upstream direction by a first check nut (26) and a nozzle holder (32) screwed to the central part (23) on the downstream side by second check nuts (33). These strength-determining components in the assembled state include a number of functional components, various seals, filters and nozzles, which will be explained hereinafter.

FIGS. 1 and 2 show the nebuliser (1) with a container (3) containing the liquid (2). The nebuliser (1) is embodied as a portable handheld device and operates without propellant gas. Preferably it may be used as a medical nebuliser for the inhalation of liquid medicament formulations.

When the liquid (2) is nebulised, an aerosol (14) is formed (FIG. 1) which, in the case of a medical nebuliser, is preferably destined for the lungs and is breathed in and optionally inhaled several times a day by a user (not shown).

After the nebuliser (1) has been opened, the container (3) holding the liquid (2) can be inserted in the nebuliser (1) from below or put in as a replacement. The container (3) forms a reservoir for the liquid (2) that is to be nebulised. Preferably, the container (3) contains sufficient liquid (2) for several doses of the liquid (2), for example up to 200 dosage units (doses) for up to 200 nebulisations or applications.

The nebuliser (1) further comprises a conveying device, particularly a pressure generator (5), for conveying and nebulising the liquid (2), in each case in a predetermined, optionally adjustable dosage quantity.

The nebuliser (1) comprises in particular a holder (6) for the container (3), an associated drive spring (7), only partly shown, preferably having a locking element (8) which can be manually actuated to release it, a hollow piston (9) embodied as a capillary, with a valve, particularly a non-return valve (10), a pressure chamber (11) and discharge nozzle (12) in the region of a mouthpiece (13). The non-return valve (10) preferably comprises a valve body which is movable in an axially restricted manner in a corresponding end recess in the hollow piston (9). In particular, the valve body is provided with a recess, groove or the like to the side and/or at the end (of the pressure chamber (11)) so that when the non-return valve (10) is opened the liquid (2) can flow around it, even if the valve body towards the pressure chamber abuts on an axial abutment of the hollow piston (9) with the non-return valve (10) open.

The container (3) is fixed in the nebuliser (1) by means of the holder 6, particularly by a locking or latching action, such that the lower end of the hollow piston (9) dips into the container (3). The holder (6) may be constructed so that the container (3) can be exchanged.

When the drive spring (7) is axially tensioned, the holder (6) with the container (3) and the hollow piston (9) is moved downwards and a dose of the liquid (2) is sucked out of the container (3) into the pressure chamber (11) of the pressure generator (5) past the non-return valve (10).

During the subsequent relaxation after the actuation of the locking element (8) the dose of liquid in the pressure chamber (11) is put under pressure by the hollow piston (9) being moved back up, with the non-return valve (10) now closed, by the release of the drive spring (7), causing it to act as a pressure piston. This pressure expels the liquid in the pressure chamber (11) out through the discharge nozzle (12), during which time it is nebulised into the preferably lung-bound aerosol (14) as shown in FIG. 1. Typically, pressure peaks of several 100 bar, in some cases up to 1200 bar, occur in the system. The cross-sectional area of the pressure chamber and the travel of the pressure piston determine the volume of liquid nebulised through the discharge nozzle. The inner volume of the high pressure chamber is preferably only slightly greater than the volume displaced by the pressure ram. Preferably, high pressure chambers with an internal volume of up to 250 microliters, particularly with volumes of between 10 and 100 microliters, are used.

The user (not shown) can inhale the aerosol (14), while preferably supply air is sucked into the mouthpiece (13) through at least one supply air opening (15).

During the nebulisation process the container (3) is moved back into its original position by the drive spring (7). It thus performs a lifting movement during the tensioning process and during the nebulisation process.

The nebuliser (1) comprises an upper housing part (16) and an inner housing part (17) which is rotatable relative thereto (FIG. 2), while a manually operable or rotatable lower housing part (18) is releasably attached, in particular, pushed onto the inner housing part (17), preferably by means of a retaining element (19). In order to insert and/or replace the container (3), the lower housing part (18) can be detached from the inner housing part (17), so that the container can be pushed axially into the inner housing part (17). The lower housing part (18) is preferably cup-shaped and engages around or over the lower free end region of the container (3).

The lower housing part (18) can be rotated relative to the upper housing part (16), whereby the inner part (17) is also rotated. In this way, the drive spring (7) is tensioned in the axial direction by means of a gear (not shown) acting on the holder (6). During tensioning the container (3) is moved axially downwards and with its end portion further into the lower housing part (18) as far as the end face thereof, until the container (3) assumes the end position shown in FIG. 2. In this state the drive spring (7) is under tension.

When tensioning first takes place, the container (3) is pierced in its base and thereby vented. An axially acting spring (20) arranged in the lower housing part (18) comes to abut on the container base (21), while the piercing element (22) mounted on the spring (20) pierces the container (3) or a seal provided in the base when contact is first made. This opens only the outer shell of the container (3), while the inner bag (4) containing the liquid (2) is not pierced. The inner volume of the bag (4) is opened by means of the hollow piston 9 which penetrates a seal at the top of the container (3) when the container (4) is inserted in the inner housing part (17), and is then inserted through a septum at the top of the container into the interior of the bag. In this way, the bag (4) in the container (3) is fluidically connected to the pressure chamber (11) via the hollow piston (9). Before the first use, after the fluidic attachment of the bag (4), the nebuliser (1) is tensioned and released several times. This process, referred to as "priming", causes the air present in the hollow piston (9) and in the pressure generator (5) up to the discharge nozzle (12) to be displaced by the liquid and the nebuliser (1) is ready for use in the intended manner. When liquid is subsequently taken out of the bag (4) through the hollow piston (9), the flexible bag (4) collapses. In order to equalise the pressure in the container (3), ambient air can flow through the vent opening into the container (3), so that the same pressure conditions are always present when the liquid (2) is being conveyed.

The pressure generator (5) has a tubular central part (23) provided with a longitudinal bore that forms the pressure chamber (11). The hollow piston (9) projects into the pressure chamber (11). It is sealed with the first seal (24) which is held by a support ring (25) and a first check nut (26) in a corresponding recess at the container end of the central part (23). In the assembled state the hollow piston (9) extends through the first seal (24) and is externally or radially sealed off thereby.

The discharge nozzle (12) is mounted at the outlet end of the central part (23). Between the discharge nozzle (12) and the pressure chamber (11) a preliminary filter (27) is preferably provided, which is preferably made of a plastic such as polyethylene or polypropylene that is chemically compatible with the liquid (2).

The preliminary filter (27) holds back particles which could block up or distort the discharge nozzle (12) or a fine filter located downstream. The filter threshold is preferably in the region of about 10 microns. Larger particles are held back from the liquid (2) flowing through by the preliminary filter (27).

In FIGS. 1 and 2 the preliminary filter (27) is held by a filter holder (28) directly at the outlet end of the pressure chamber (11), for example by pressing, while the filter holder (28) is sealed off from the central part (23) by means of a second seal (29), particularly an O-ring. However, other design solutions are also possible, as will be shown for example in another embodiment (cf. also FIG. 3 hereinafter).

Preferably, a very fine filter and the discharge nozzle (12) are located directly after the preliminary filter (27) or the filter holder (28). A two-stage filtering of the liquid through the preliminary filter (27) and very fine filter before nebulisation is particularly preferred. In particular, the very fine filter and discharge nozzle (12) form a single component. Using the very fine filter, particles are filtered out which could block or displace the very fine outlet channels of the discharge nozzle (12). The filter threshold is in particular at 2-5 microns.

The discharge nozzle (12) is preferably received and radially held by a nozzle seal (30). A nozzle holder (32) is attached on the outlet side. For attachment to the central part (23), the second check nut (33) is provided. The nozzle holder (32) holds the discharge nozzle (12) and the nozzle seal (30).

The discharge nozzle (12) is made up of two parts fixedly attached to one another, the first plate (12*a*) and second plate (12*b*), which are made of glass and/or silicon. One plate is microstructured and contains, on a flat side, a flow region which connects the nozzle inlet to the nozzle outlet. The two plates (12*a*) and (12*b*) are preferably joined firmly together by bonding. The flow region with the nozzle inlet located upstream and the nozzle outlet located downstream is enclosed between the two plates. The microstructures located between the plates first of all form a very fine filter structure in the flow region in the direction of flow and then form the nozzle channel with nozzle outlet. This very fine filter structure is formed for example by narrow channels through walls and/or elevations with a specified surface density. The volume of the fluidic connection to the discharge nozzle (12) adjoining the pressure chamber (11) and the volume of the discharge nozzle (12) itself are as small as possible in order to achieve a small dead volume. The flow resistance through the discharge nozzle (12) is substantially higher than the flow resistance of the liquid (2) flowing through the hollow piston into the pressure chamber (11) during the tensioning stroke, so that the nebuliser operates without any valve on the outlet side in the nozzle region.

The nebuliser operates with a spring pressure of 50-600 bar, preferably 100-500 bar. On each actuation of the nebuliser, a liquid volume of 10-50 microliters is delivered. The liquid is converted into an aerosol, the droplets of which have an aerodynamic diameter of up to 20 microns, preferably 3-10 microns. The associated nozzles produce a nozzle spray spread of from 20° to 160°, preferably from 80° to 100°. These magnitudes apply to the nebuliser according to the teaching of the present invention as particularly preferred values.

FIG. 3 shows, by way of example, a schematic section through a high pressure chamber (100) according to the invention, of the kind that may be used in a nebuliser according to FIGS. 1 and 2, for example.

The strength-determining components of the high pressure chamber (100) are a central part (123), which is substantially cylindrical on the inside, and the components that close off this central part at both ends, namely the nozzle holder (133) and the support ring (126). In the assembled state, these components may enclose further components such as seals, filters and nozzles in the system.

The central part (123) shown as a special embodiment in FIG. 3 comprises a central part base member (123*a*), here a metallic base member (123*a*), which has on the inside a substantially cylindrical cross-section and an outer shape which is adapted to the shape of the strength-determining components connected thereto, namely the support ring (126) and nozzle holder (133); central part second material region (123*b*) which is fixedly connected to the central part base member (123*a*); and a central part connecting ring (123*c*) downstream from the central part (123). These connecting regions may have both raised and lowered structures such as, for example, webs, projections, beads, holes or groove-like depressions, or slot-like recesses. In the embodiment shown in FIG. 3 there are rectangular split- or slot-like recesses extending parallel to the longitudinal direction of the central part (123), in which connecting elements provided on components (126) and (133) engage by positive locking. Connecting elements of two or more components may engage in a single recess of this kind. In FIG. 3, in each case, a support ring connecting element (126*c*) of the support ring (126) engages in the same recess as a nozzle holder connecting element (133*c*) of the nozzle holder (133). However, other design solutions are possible, particularly with regard to the shape of the connecting points, the number of connecting elements engaging at each connecting point and the number of components that engage by means of connecting elements at a connecting point. For example, there may be in each case only one connecting element or alternatively two or more connecting elements may be attached to a connecting point. One or more other components may be attached to one component. In addition to the connecting elements with the strength-determining components of the high pressure chamber (100), other connecting elements may be moulded on directly to the outside of the central part (123) or to the components (126) or (133), in order to install the entire high pressure chamber (100) in a total system such as a nebuliser. Particularly preferably, these additional connecting elements may be spring arms (123*d*) which bring about a spring latching or snap-fit connection to other components.

The central part (123) may also comprise a central part second material region (123*b*) which is fixedly connected to the central part base member (123*a*), while this region may consist of a different material, preferably a plastic. This central part second material region (123*b*) may cover all the surfaces that are in contact with the liquid during operation throughout the entire system. Preferably, a plastic material is used which is chemically compatible with the liquid used, to ensure that there is no material corrosion and no change in the liquid such as, for example, a break down of active substance. Suitable plastics include for example polyethylene or polypropylene. Such plastics may also be used for example for the second material regions at the liquid end described hereinafter which are provided on other components such as the support ring (126) and nozzle holder (133).

The second material region—for example the central part second material region (123*b*)—may be a coating, the surface of which extends substantially parallel to the surface of the underlying base member, for example the central part base member (123*a*). In addition, the second material region may be attached to the base member, for example the central part base member (123*a*), by injection-moulding, gluing, bonding, snap-fitting or similar methods of attachment. In particular, using bonding methods as mentioned above, the second material region may have a shape which is different from the shape of the base member. FIG. 3 shows a central part (123) in which a central part second material region (123*b*) preferably injection-moulded onto the central part base member (123*a*) extends with individual structures over the entire inner region of the central part (123).

The central part second material region (123*b*) serves as a support surface for other components which may be included when the components that determine the strength of the high pressure chamber (100) are assembled, namely the central part (123), support ring (126) and nozzle holder (133). The structure of the central part second material region (123*b*) determines the position of installation of separate filters such as a preliminary filter (27) and another fine filter (31). These filters may be pushed in, by press-fitting in a partly conical shape, from the upstream end of the central part (123) against an annular collar or abutment in the inner structure of the second material region (123*b*). With this type of construction there is no need for any further components to act as a filter holder or as a seal in the region of the filters. The filter threshold of the fine filter (31) is chosen such that it is between that of the preliminary filter (27) and that of the very fine filter integrated in the discharge nozzle (12).

Other designs regarding the filter installation, the types of filters, number of filters and the sequence of filters are possible. The structures of the central part second material region (123*b*) prevent any contact between the liquid and the central part base member (123*a*). The seals with other components may abut on the central part second material region (123*b*) such that there is no direct contact between the central part base member (123*a*) and the seal. The first seal (24), for example an O-ring, seals off the central part (123) and the support ring (126) from the hollow piston (9). The first seal (24) is located in a recess provided in the central part second material region (123*b*). The central part second material region (123*b*) projects with a central part connecting ring (123*c*) downstream from the central part (123) and forms the support surface for the nozzle seal (12).

The support ring (126) shown in FIG. 3 forms, with the first seal (24) and the pressure generator (5), the upstream boundary of the high pressure chamber (100). Similarly to the central part (123), the support ring (126) may be made of different material regions which are firmly attached to one another analogously: a support ring base member (126*a*) and directly attached thereto a support ring second material region (126*b*), which is chemically compatible with the liquid. As with the central part (123), the shape of the support ring (126) determines the attachment to at least one other component, in this case the central part (123): the support ring (126) contains, in its support ring base member (126*a*), which determines its strength, support ring connecting elements (126*c*) which protrude in the direction of the component that is to be attached and are connected in a positively locking manner to the corresponding connecting forms on the central part (123) by a forming process. The protruding connecting elements may take various forms: webs of different thicknesses, widths and lengths in various numbers, with encircling collars or tubular projections which may be folded over in the manner of a flange, or zig-zag rings which may abut inwardly or outwardly on mating contours in the manner of a crown cork crimping. The support ring connecting elements (126*c*) may preferably be distributed in groups (at least two, preferably four or more) uniformly over the circumference of the support ring (126). These strips or arms pointing downstream are bent inwardly by a shaping process such as crimping into corresponding recesses on the central part (123) and form a solid, positively locking connection between the two components, namely the support ring (126) and the central part (123). The shape of the crimped connection and the dimensions of the crimp arms are dependent on the material used for the central part base member (123*a*) and the pressures that are to be withstood within the system. With suitable shapes and materials for the crimps, the components joined together are capable of withstanding an internal pressure of 5000 bar. Particularly preferred are support ring connecting elements (126*c*) in the form of four protruding cuboid arms uniformly distributed over the edge of the component, with a width of between 0.8 and 1.8 mm, a length of between 1.6 and 3.0 mm and a material thickness of between 1.5 and 2.5 mm. If the number of arms is changed, their width must be adapted, in particular; thus if there are only two arms a width of between 1.6 and 3.6 mm would be preferred.

Comparable in terms of operating principle but not shown in the drawings, protruding connecting elements are provided on the central part (123), which are shaped so as to engage positively in corresponding recesses on at least one of the other strength-determining components ((126) or (133)).

Analogously to the central part second material region (123*b*) of the central part (123), the support ring second material region (126*b*) of the support ring (126) may be a coating, on the one hand, the surface of which extends substantially parallel to that of the underlying central part base member (123*a*). On the other hand, the support ring second material region (126*b*) may be attached to the support ring base member (126*a*) by spraying on, gluing, bonding, snap-fitting or similar methods of attachment and have a suitable shape which is outwardly different from the support ring base member (126*a*). FIG. 3 shows a support ring (126) in which a support ring second material region (126*b*) sprayed onto the support ring base member (126*a*) with a structure which is outwardly different from the support ring base member (126*a*) extends over the entire region of the support ring (126) oriented towards the central hollow piston (9). As a result, on the one hand, as in the central part (123), all direct contact between the liquid (2) and the support ring base member (126a) is prevented. On the other hand, the metallic hollow piston (9) with the non-return valve (10) installed at the pump end cannot touch the support ring member (126a) at any time, i.e. not even during assembly. This prevents damage during assembly. Furthermore, the support ring second material region (126b) may be provided with insertion slopes and/or have special slipping qualities to assist with the mounting of the hollow piston.

The support ring second material region (126b) is also a contact surface for the first seal (24) of the high pressure chamber (100). The first seal (24) is enclosed in the system during the assembly of the components that are the central part (123) and support ring (126). The support ring second material region (126b) projects into the central part (123) which forms a receiving socket for the first seal (24). Thus, the first seal (24) does not make any direct contact with the support ring base member (126a). Any liquid passing through the sealing member within the high pressure chamber (100) does not make any contact with the material of the support ring base member (126a).

If necessary, in addition to filters ((27) and (31)) or first seal (24), other components may be enclosed by the assembly of the central part (123) and support ring (126), e.g. a spacer (36) in the form of a flat washer with a central bore. With the thickness of the spacer (36) the depth of penetration of the support ring second material region (126b) into the central part (123) can be varied. Thus, the degree of compression and the pretensioning of the first seal (24) can be adjusted.

In another embodiment of the high pressure chamber which is not shown in the figures, the sealing function of a sealing element—such as one of the first seal (24) or second (29) or the nozzle seal (30)—can be taken over by a second material region on one of the strength determining components comprising the central part (123), the support ring (126) or the nozzle holder (133). The second material region may consist of a standard commercial elastomer such as silicon and may be connected to the respective central part base member (123a) or support ring base member (126a) analogously to the material composites described above with reference to the central part (123) and support ring (126).

In another embodiment of the high pressure chamber, which is not shown in the figures, the number of strength-determining components can be reduced from three to two. For this, the central part (123) may be combined with either the support ring (126) or the nozzle holder (133) to form a single component. This can be done by attaching seals by injection moulding. If the function of the first seal (24) is taken over by the central part second material region (123b)—e.g. consisting of an elastomer—of the central part, the counter-holder of this seal formed by the support ring (126) in FIG. 3 is no longer required.

Figure 3:
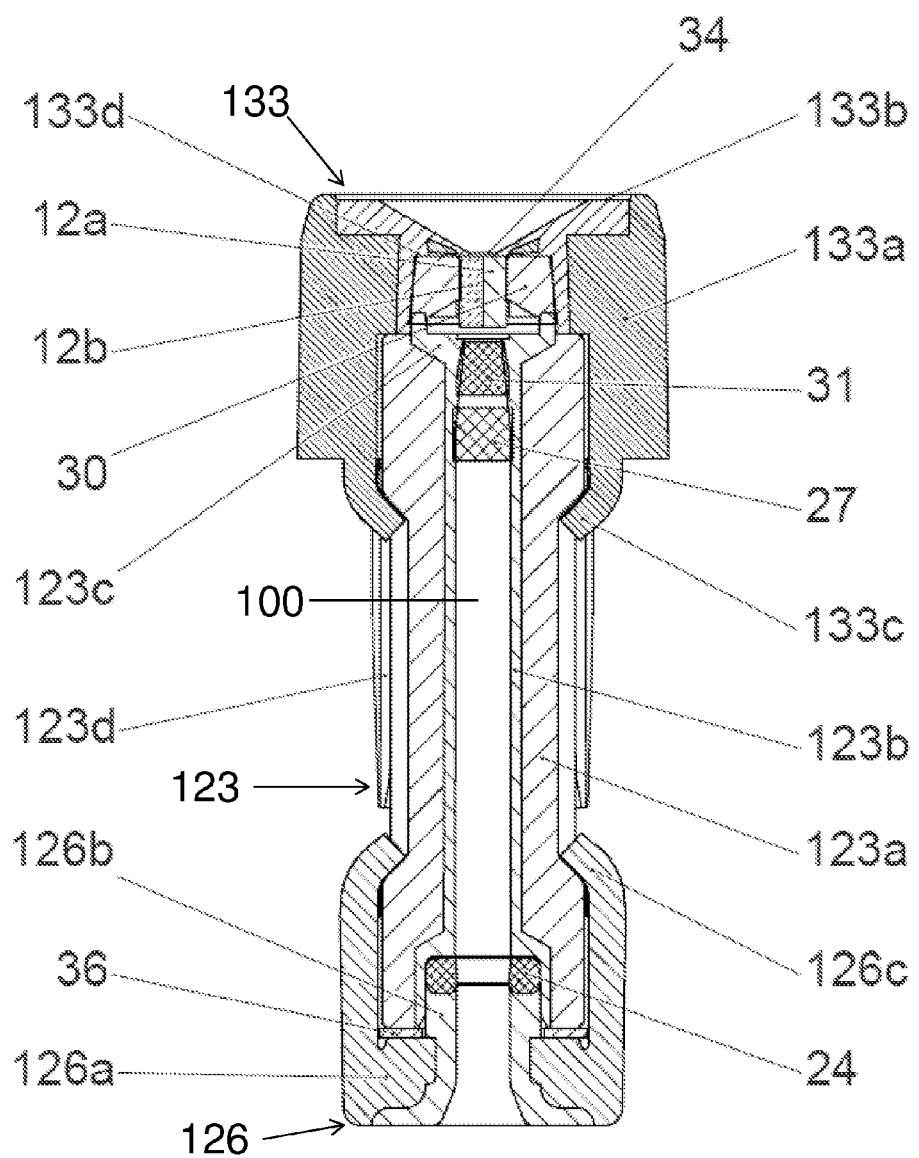
FIG. 3 is a schematic section through the high pressure chamber according to the invention for use in a nebuliser.

The nozzle holder (133) shown in FIG. 3 forms, with the nozzle seal (30) and the discharge nozzle (12), the downstream boundary of the high pressure chamber (100). Like the central part (123) and the support ring (126), the nozzle holder (133) comprises two material regions: a nozzle holder strength-determining base member (133a) and a nozzle holder second material region (133b) attached directly, which is chemically compatible with the liquid (2). As with the central part (123) and the support ring (126), the attachment to the central part (123) is determined by the shape of the nozzle holder (133): the nozzle holder (133) comprises nozzle holder connecting elements (133c) on the nozzle holder base member (133a), which project towards the component that is to be attached, these connecting elements being connected to the corresponding shapes on the central part (123) in a positively locking manner by forming. The projecting connecting elements may consist of a variety of geometrical shapes: webs of different widths, thicknesses, lengths and numbers, encircling collars or tubular projections which can be folded over in the manner of a flange, zig-zag rings which abut inwardly on mating contours in the manner of a crown cork crimping. The nozzle holder connecting elements (133c) may be a plurality (at least two, preferably four or more) of webs or arms pointing upstream and uniformly distributed over the circumference of the nozzle holder (133). During the shaping, e.g. in the course of a crimping process, the connecting elements are pressed into corresponding recesses on the central part (123). This produces a positively locking and firm connection between the two components. The design of the nozzle holder connecting elements (133c) corresponds to those on the supporting ring (126): particularly preferred are nozzle holder connecting elements (133c) in the form of four protruding cuboid arms uniformly distributed over the edge of the component, with a width of between 0.8 and 1.8 mm, a length of between 1.6 and 3.0 mm and a material thickness or thickness of between 1.5 and 2.5 mm. If the number of arms is changed their width must be adapted, in particular; thus, if there were only two arms, a width of between 1.6 and 3.6 mm would be preferred.

The nozzle holder second material region (133b) of the nozzle holder (133) may be designed analogously to the central part second material region (123b) of the central part (123) and to the support ring second material region (126b) of the support ring (126), on the one hand, in the form of a coating in which the surface of the nozzle holder second material region (133b) extends substantially parallel to that of the underlying nozzle holder base member (133a). On the other hand, the second material region may be attached to the nozzle holder base member (133a) by injection moulding, gluing, bonding, snap-fitting or other methods.

The use of a metal injection moulding process is preferred for the manufacture of the base members of the strength-determining components of the high pressure chamber (100), namely the nozzle holder (133), central part (123) and support ring (126).

Figure 4A:
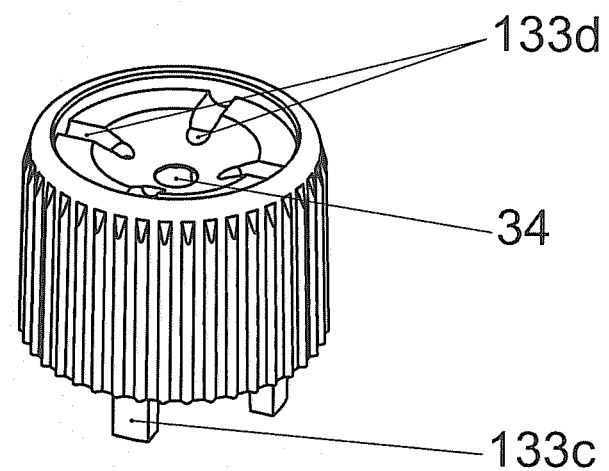
FIG. 4a shows the base member of a component (nozzle holder) of the high pressure chamber from FIG. 3 before the attachment of a second material zone and before assembly.
Figure 4B:
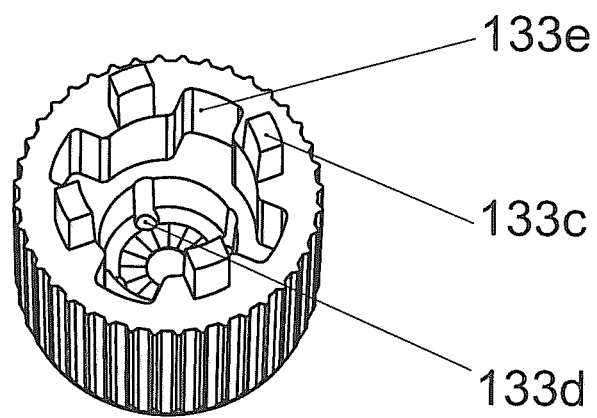
FIG. 4b shows the same base member from FIG. 4a from a different perspective.
Figure 5:
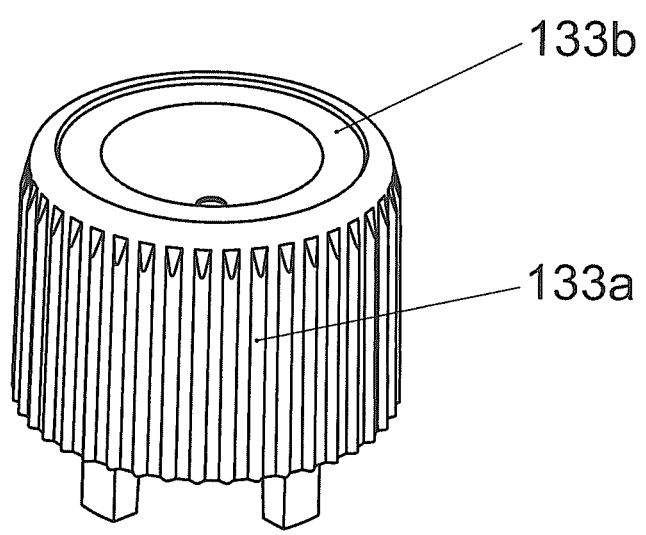
FIG. 5 shows the finished component from FIG. 4 including the attached second material zone before attachment to the high pressure chamber.

FIGS. 4 and 5 show a nozzle holder (133) which can be inserted in a high pressure chamber (100) according to FIG. 3, at various stages of manufacture: the nozzle holder base member (133a) produced by the MIM process is shown in FIGS. 4a and 4b in two perspectives. The shape of the nozzle holder base member (133a) is adapted to the subsequent process and assembly steps: the injection moulding of a second material region, attachment to other components and securing by a crimping process.

For injection-moulding the second material region of plastics, flow channels (133d) are provided in the nozzle holder base member (133a). The nozzle holder base member (133a) is placed as an insert in the mould of an injection moulding machine. The liquefied injection moulding composition is distributed uniformly through the flow channels over the areas of the base member that are to be coated. Flow channels (133d) running parallel to the axis of the through-bore (34) allow material to be injected simultaneously on opposite surfaces of the nozzle holder base member (133a). After assembly, the through-bore (34) exposes the outlet opening of the discharge nozzle (12). The nozzle holder second material region (133b) is configured so that there cannot be any contact between the liquid (2) and the nozzle holder base member (133a). This may relate not only to the liquid (2) contained in the high pressure chamber (100) but also to the aerosol (4)

emerging from the nozzle, the mist of which might wet the nozzle holder (133) in the upper area.

Using the possibilities of metal and plastics injection moulding technology which are known to the skilled man, other embodiments are possible, not shown here, in which the surface of the nozzle holder (133) at the aerosol end can be continued to the through-bore (34) by other channels which open upwardly and to the side of the holder. When sidestream air is sucked into the interior of the mouthpiece (13) though the supply air openings (15) as the patient breathes in, this sidestream air can be brought to the point of origin of the aerosol (14) through the new channels, where it acts as an enveloping flow. In this way, the alignment of the aerosol mist can be further assisted and the depositing of aerosol particles on the nozzle holder (133) or inside the mouthpiece (13) can be reduced.

If desired, an oriented assembly of the nozzle holder (133) may be provided during attachment to the central part (123) by means of a positioning aid on the nozzle holder (133e). This positioning aid on the nozzle holder (133e) may be made in any desired shape, using contours provided at the point of attachment, provided that it is a negative to the corresponding contour of the component that is to be attached. If orientation-free attachment is desired, the contour at the point of attachment may for example be in the form of an azimuthal groove in which the corresponding crimping engages.

Additionally, the outer surface of the nozzle holder base member (133a) and hence of the nozzle holder (133) may comprise gripping surfaces and insertion slopes for the following process steps. A gripping surface of this kind is shown in FIGS. 4 and 5 in the form of an encircling rifling of the nozzle holder base member (133a). In FIGS. 4a and 4b the nozzle holder connecting elements (133c) are shown in the form of four crimping arms. These straight crimping arms are bent inwardly in the subsequent attachment process and abut in a positively locking manner in corresponding recesses on the central part (123) attached thereto. In the embodiment shown in FIG. 3, the components consisting of the discharge nozzle (12) and nozzle seal (30) are enclosed in the high pressure chamber (100) by the joining and connecting of the nozzle holder (133) and central part (123). The discharge nozzle (12) forms the downstream closure of the high pressure chamber (100). So that the central part (123) is sealed off from the nozzle holder (133) and the liquid does not touch the nozzle holder base member (133a) of the nozzle holder (133), the discharge nozzle (12) abuts only on the nozzle holder second material region (133b) of the nozzle holder (133), analogously to the components enclosed by the central part (123) and support ring (126). In the case of brittle materials used for the nozzle holder or delicate microstructures, this has the advantage that during insertion, the nozzle holder meets a surface that is softer than the rigid base nozzle holder member (133a) and consequently damage to the nozzle holder during installation, for example, is avoided.

The preferred manufacturing process for the components that determine the strength of the high pressure chamber (100), namely the central part (123) and support ring (126) and nozzle holder (133), and the attachment of these components will once again be summarised schematically:

preparation of a granulated mixture of a metal powder and a binder injection of the molten granulated mixture into a mould in an injection moulding machine removal of the rough casting from the mould elimination of binders from the rough casting (e.g. by heat treatment)

sintering of the rough casting and recovery of the respective base member (123a), (126a) or (133a) made of sintered metal preparation of plastics granules placing a base member in a mould in an injection moulding machine injection of the molten plastic into the mould in the injection moulding machine removal of the composite component (123), (126) or (133) from the mould optionally placing components in a composite component (e.g. nozzle seal (30) with discharge nozzle (12) in the nozzle holder (133); fine filter (31), preliminary filter (27) and first seal (24) in the central part (123))

joining the components that determine the strength of the high pressure chamber to one another joining the assembled components by shaping the connecting elements, particularly by crimping crimp arms.

For the choice of material for components from an MIM process (particularly for components with connecting elements that are to be shaped, such as support ring base member (126a) or nozzle holder (133a) from FIG. 3), it is preferable to select metals in which the material is strengthened by the forming or crimping and the compressive strength of the high pressure system is increased. One of many examples of a metal of this kind is the stainless steel US-AISA 317F, as may be obtained from Messrs Strack of Germany. This metal can be cold-crimped without any additional input of heat from outside.

Crimped joints are permanent joints, i.e. they cannot be undone without damaging the components. A crimp joint can certainly be opened by carefully bending back the crimp arms, but because of the solidification of the material during the first crimping the crimp arms cannot be returned to their original state, even if they can be bent back without breaking. When a crimp joint is opened, at least material wear or changes to the material must be expected.

Depending on the demands made of the components and the complexity of the components and systems, this manufacturing process may be modified almost at will in accordance with methods which are fundamentally known to the skilled man. Thus, additional requirements of a component or the system may be met by means of a third material region on selected components if another set of process steps for coating or injection-coating components is included.

The strength-determining components of the high pressure pump may originate from different processes. For example, the central part (23) may consist directly of a high grade plastics such as the comparatively expensive PEEK (polyether-ether-ketone) depending entirely on the demands and material costs.

The strength-determining components may consist of a material other than metal or sintered metal. Instead of manufacturing the base member in the MIM process, the central part (123) may consist of a drawn tube which provides strength. The tube may be placed as an insert in an injection moulding machine. The structures located on the inside and outside may be moulded to the tube in a plastics injection moulding process.

The present invention has the following advantages:

economical mass production of precision components from sintered metal varied complicated shapes of the components can be obtained almost without any additional production costs connecting elements and positioning aids contained within the shape of the components enable the components to be assembled rapidly and economically components joined together by crimping are capable of withstanding a liquid pressure of up to 5000 bar crimp joints are less prone to failure than screw joints in terms of their positional tolerances.

the shape of the sintered metal components is not restricted to rotationally symmetrical shapes.

as the sintered metal it is possible to use metals that are difficult to process by known methods.

all kinds of demands on the material of a component (rigidity, robustness, compatibility, corrosion resistance) can be met by two-component injection moulding compact construction of the high pressure chamber suitable for use in handheld devices limited dead space thanks to internal coating and reducing the size of the components of the high pressure chamber avoidance of damage when assembling components inside the high pressure chamber thanks to coating with plastics If the high pressure chamber according to the invention is used in the medical field the liquid (2) is preferably a medicament preparation.

Some preferred compounds or pharmaceutical active substances, ingredients and/or formulations of medicinal liquids are listed below. Any desired mixtures with a range of other liquids may be used. Powdered substances may be dissolved either in water or in any desired solvent or may be present in the form of a suspension.

The pharmaceutical compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{[4-(2-hydroxy-2-phenyl-ethylamino)-phenyl]ethylamino}-ethyl)-benzaldehyde N-[2-hydroxy-5-(1-hydroxy-2-{2-[4-(2-hydroxy-2-phenyl-ethylamino)-phenyl]ethylamino}-ethyl)-phenyl]formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]urea 4-(2-{6-[2-(2,6-dichloro-benzyloxy)-ethoxy]hexylamino}-1-hydroxy-ethyl)-2-hydroxymethyl-phenol 3-(4-{6-[2-hydroxy-2-(4-hydroxy-3-hydroxymethyl-phenyl)-ethylamino]hexyloxy}-butyl)-benzylsulphonamide 3-(3-{7-[2-hydroxy-2-(4-hydroxy-3-hydroxymethyl-phenyl)-ethylamino]heptyloxy}-propyl)-benzylsulphonamide 4-(2-{6-[4-(3-cyclopentanesulphonyl-phenyl)-butoxy]hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

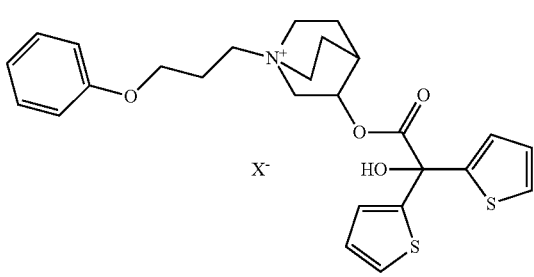

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

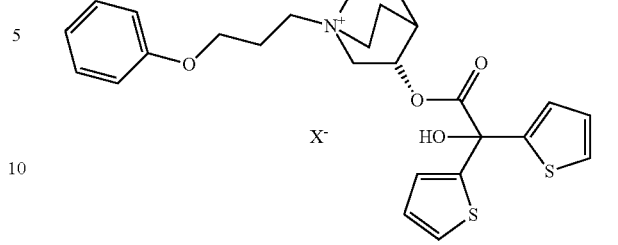

AC-1-en wherein X⁻ may have the above-mentioned meanings. Other preferred anticholinergics are selected from the salts of formula AC-2

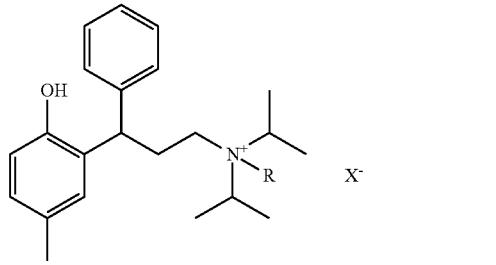

AC-2 wherein R denotes either methyl or ethyl and wherein X⁻ may have the above-mentioned meanings. In an alternative embodiment the compound of formula AC-2 may also be present in the form of the free base AC-2-base.

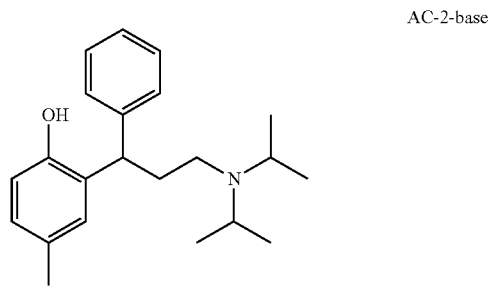 [SMILES: Cc1ccc(O)c(C(CCN(C(C)C)C(C)C)c2ccccc2)c1]

AC-2-base

Other specified compounds are:
tropenol 2,2-diphenylpropionate methobromide
scopine 2,2-diphenylpropionate methobromide
scopine 2-fluoro-2,2-diphenylacetate methobromide
tropenol 2-fluoro-2,2-diphenylacetate methobromide
tropenol 3,3',4,4'-tetrafluorobenzilate methobromide
scopine 3,3',4,4'-tetrafluorobenzilate methobromide
tropenol 4,4'-difluorobenzilate methobromide
scopine 4,4'-difluorobenzilate methobromide
tropenol 3,3'-difluorobenzilate methobromide
scopine 3,3'-difluorobenzilate methobromide
tropenol 9-hydroxy-fluorene-9-carboxylate methobromide
tropenol 9-fluoro-fluorene-9-carboxylate methobromide
scopine 9-hydroxy-fluorene-9-carboxylate methobromide
scopine 9-fluoro-fluorene-9-carboxylate methobromide
tropenol 9-methyl-fluorene-9-carboxylate methobromide
scopine 9-methyl-fluorene-9-carboxylate methobromide cyclopropyltropine benzilate methobromide
cyclopropyltropine 2,2-diphenylpropionate methobromide
cyclopropyltropine 9-hydroxy-xanthene-9-carboxylate methobromide
cyclopropyltropine 9-methyl-fluorene-9-carboxylate methobromide
cyclopropyltropine 9-methyl-xanthene-9-carboxylate methobromide
cyclopropyltropine 9-hydroxy-fluorene-9-carboxylate methobromide
cyclopropyltropine methyl 4,4'-difluorobenzilate methobromide
tropenol 9-hydroxy-xanthene-9-carboxylate methobromide
scopine 9-hydroxy-xanthene-9-carboxylate methobromide
tropenol 9-methyl-xanthene-9-carboxylate methobromide
scopine 9-methyl-xanthene-9-carboxylate methobromide
tropenol 9-ethyl-xanthene-9-carboxylate methobromide
tropenol 9-difluoromethyl-xanthene-9-carboxylate methobromide
scopine 9-hydroxymethyl-xanthene-9-carboxylate methobromide The above-mentioned compounds may also be used as salts within the scope of the present invention, wherein instead of the methobromide the metho-X salts are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6,9-difluoro-11-hydroxy-16-methyl-3-oxo-17-(2,2,3,3-tertamethylcyclopropylcarbonyl)oxy-androsta-1,4-diene-17-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxyphenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]quinazoline 4-[(3-chloro-4-fluoro-phenyl)amino]-6-{2-[4-(2-oxo-morpholin-4-yl)-piperidin-1-yl]ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy]-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxy-ethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

As pharmaceutically active substances, substance formulations or substance mixtures, any inhalable compounds may be used, also including inhalable macromolecules as disclosed in EP 1 003 478. Preferably, substances, substance formulations or substance mixtures are used to treat respiratory complaints, which are used by inhalation.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of reference numerals | |
| --- | --- |
| 1 | nebuliser |
| 2 | liquid |
| 3 | container |
| 4 | bag |
| 5 | pressure generator |
| 6 | holder |
| 7 | drive spring |
| 8 | locking element |
| 9 | hollow piston |
| 10 | nonreturn valve |
| 11 | pressure chamber |
| 12 | discharge nozzle |
| 12a | plate |
| 12b | plate |
| 13 | mouthpiece |
| 14 | aerosol |
| 15 | supply air opening |
| 16 | upper housing part |
| 17 | inner housing part |
| 18 | lower housing part |
| 19 | retaining element |
| 20 | spring (in lower housing part) |
| 21 | container base |
| 22 | piercing element |
| 23 | central part |
| 24 | first seal |
| 25 | support ring |
| 26 | first check nut |
| 27 | preliminary filter |
| 28 | filter holder |
| 29 | second seal |
| 30 | nozzle seal |
| 31 | fine filter |
| 32 | nozzle holder |
| 33 | second check nut |
| 34 | through-hole |
| 36 | spacer |
| 100 | high pressure chamber |
| 123 | central part |
| 123a | central part base member |
| 123b | central part second material region |
| 123c | central part connecting ring |
| 123d | spring arm |
| 126 | support ring |
| 126a | support ring base member |
| 126b | support ring second material region |
| 126c | support ring connecting element |
| 133 | nozzle holder |
| 133a | nozzle holder base member |
| 133b | nozzle holder second material region |
| 133c | nozzle holder connecting element |
| 133d | flow channel |
| 133e | positioning aid on the nozzle holder |

Note:
For numbers 37-99 there are no reference numerals in the figures

The invention claimed is:

1. High pressure chamber in the form of a multi-part pumping chamber with nozzle outlet (12), in which a liquid (2) is placed under pressure up to 5000 bar,
wherein said chamber comprises a central part (123), a nozzle holder (133) and a support ring (126), wherein at least one of said central part (123), nozzle holder (133) and support ring (126) consists of a metal,
wherein the at least one of said central part (123), nozzle holder (133) and support ring (126) that consists of a metal is at least partly covered by a second material region, wherein the second material region comprises at least one of a central part second material region (123*b*) directly injection-molded onto the central part (123), a nozzle holder second material region (133*b*) directly injection-molded onto the nozzle holder (133), and a support ring second material region (126*b*) directly injection-molded onto the support ring (126), and
wherein on the at least one of said central part (123), nozzle holder (133) and support ring (126) that consists of a metal, the second material region forms all surfaces that are in direct contact with the liquid during operation of the chamber.

2. High pressure chamber according to claim 1, wherein the second material region comprises a material that is corrosion-resistant and/or pharmaceutically compatible with the liquid (2) provided for use.

3. High pressure chamber according to claim 1, wherein the material of the second material region is a plastic selected from polypropylene and polyethylene.

4. High pressure chamber according to claim 1, wherein the second material region (123*b*, 126*b*, 133*b*) by virtue of its shape and its material nature, at the junction point of the central part (123) and the nozzle holder (133) or at the junction of the central part (123) and the support ring (126), constitutes a seal for the interior of the high pressure chamber.

5. High pressure chamber according to claim 1, wherein on the nozzle outlet side of the nozzle holder (133) there is at least one channel running therethrough which is open at the top.

6. High pressure chamber in the form of a multi-part pumping chamber with nozzle outlet (12), in which a liquid (2) is placed under pressure up to 5000 bar, and at least one component of the chamber consists of a metal capable of being shaped and/or crimped and is permanently connected to at least one other component of the chamber in a positively locking manner by shaping or crimping, wherein the nature of the connection of the metal component that is to be joined to another component, or the configuration of the crimping, are already predetermined by the shape of support ring connecting element (126*c*), nozzle holder connecting element (133*c*), and spring arm (123*d*) on the metal component, and in that the support ring connecting element (126*c*) and nozzle holder connecting element (133*c*) are connected to another component by crimping and take the form of at least two webs or arms bent towards the other component.

7. High pressure chamber according to claim 6, wherein the crimpable metal additionally has the property that the material is strengthened by mechanical forming.

8. High pressure chamber according to claim 6, wherein separate individual components which have sealing and/or filtering and/or liquid-nebulising and/or adjusting functions are enclosed in the high pressure chamber by forming or crimping.

9. High pressure chamber according to claim 6, wherein the webs or arms (support ring connecting element (126c), nozzle holder connecting element (133c)) that are bent during crimping have a width of between 0.8 and 3.6 millimeters and/or a length of between 1.6 and 3.0 millimeters and a material thickness of between 1.5 and 2.5 millimeters.

10. High pressure chamber according to claim 6, wherein the internal capacity of the chamber is 10 to 100 microliters, and/or the high pressure chamber is designed for an excess pressure range of up to 1200 bar.

11. High pressure chamber according to claim 6, further comprising at least one nozzle holder (32,133) and/or a central part (23, 123) and a support ring (25, 126), wherein in one process step at least two of the components are inserted one inside the other and joined together by forming or crimping.

12. High pressure chamber according to claim 11, wherein at least one of the components nozzle holder (133), central part (123) or support ring (126) is provided with a second material region comprising central part second material region (123b), support ring second material region (126b), and nozzle holder second material region (133b), a coating or lining, before the crimping, in a separate injection-moulding process.

13. High pressure chamber according to claim 6, wherein a second material region comprising at least one of a central part second material region (123b), a nozzle holder second material region (133b), and a support ring second material region (126b) is directly injection-molded onto at least one metal component.

14. High pressure chamber according to claim 13, wherein the second material region covers all the surfaces of the metal component that are in direct contact with liquid during operation of the chamber, wherein the second material is selected so that it is corrosion-resistant and/or pharmaceutically compatible with the liquid (2) provided for use.

15. High pressure chamber according to claim 6, wherein the at least one metal component is produced by metal injection molding methods.

16. High pressure chamber according to claim 6, wherein the central part (123) is combined with the support ring (126) to form a single component.

17. High pressure chamber according to claim 6, wherein the central part (123) is combined with the nozzle holder (133) to form a single component.

18. Nebulizer (1) or injector for nebulizing or injecting a liquid (2) medicament formulation, having a high pressure chamber according to claim 6.

19. High pressure chamber in the form of a multi-part pumping chamber with nozzle outlet (12), in which a liquid (2) is placed under pressure up to 5000 bar,
wherein said chamber comprises at least two of a central part (123), a nozzle holder (133) and a support ring (126), wherein at least one of said at least two of a central part (123), nozzle holder (133) and support ring (126) consists of a metal,
wherein the at least one of said at least two of a central part (123), nozzle holder (133) and support ring (126) that consists of a metal is at least partly covered by a second material region, wherein the second material region comprises at least one of a central part second material region (123b) directly injection-molded onto the central part (123), a nozzle holder second material region (133b) directly injection-molded onto the nozzle holder (133), and a support ring second material region (126b) directly injection-molded onto the support ring (126), and
wherein on the at least one of said at least two of a central part (123), nozzle holder (133) and support ring (126) that consists of a metal, the second material region forms all surfaces that are in direct contact with the liquid during operation of the chamber.

20. High pressure chamber according to claim 19, wherein the second material region comprises a material that is corrosion-resistant and/or pharmaceutically compatible with the liquid (2) provided for use.

21. High pressure chamber according to claim 19, wherein the material of the second material region is a plastic selected from polypropylene and polyethylene.

22. High pressure chamber according to claim 19, wherein the second material region (123b, 126b, 133b) by virtue of its shape and its material nature, at the junction point of the central part (123) and the nozzle holder (133) or at the junction of the central part (123) and the support ring (126), constitutes a seal for the interior of the high pressure chamber.

23. High pressure chamber according to claim 19, wherein on the nozzle outlet side of the nozzle holder (133) there is at least one channel running therethrough which is open at the top.

* * * * *